(12) United States Patent
Maddaloni et al.

(10) Patent No.: US 12,005,110 B2
(45) Date of Patent: Jun. 11, 2024

(54) **HONEYBEE COMMENSAL *SNODGRASSELLA ALVI* VACCINE AGAINST PATHOGENIC *NEISSERIACEAE***

(71) Applicant: UNIVERSITY OF FLORIDA RESEARCH FOUNDATION, INCORPORATED, Gainesville, FL (US)

(72) Inventors: Massimo Maddaloni, Gainesville, FL (US); David Wayne Pascual, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 220 days.

(21) Appl. No.: 17/431,281

(22) PCT Filed: Feb. 14, 2020

(86) PCT No.: PCT/US2020/018208
§ 371 (c)(1),
(2) Date: Aug. 16, 2021

(87) PCT Pub. No.: WO2020/168146
PCT Pub. Date: Aug. 20, 2020

(65) Prior Publication Data
US 2022/0125908 A1     Apr. 28, 2022

Related U.S. Application Data

(60) Provisional application No. 62/805,896, filed on Feb. 14, 2019.

(51) Int. Cl.
| | | |
|---|---|---|
| *A61K 39/02* | (2006.01) | |
| *A61K 39/095* | (2006.01) | |
| *A61K 45/06* | (2006.01) | |
| *A61P 31/04* | (2006.01) | |
| *A61K 39/00* | (2006.01) | |

(52) U.S. Cl.
CPC ............ *A61K 39/095* (2013.01); *A61K 45/06* (2013.01); *A61P 31/04* (2018.01); *A61K 2039/522* (2013.01); *A61K 2039/545* (2013.01)

(58) Field of Classification Search
None
See application file for complete search history.

(56) References Cited

U.S. PATENT DOCUMENTS

| 7,585,510 B1 | 9/2009 | Plested et al. |
| 9,844,601 B2 | 12/2017 | Ryall |
| 11,690,387 B2 * | 7/2023 | Martinez ............... A23K 50/90 800/8 |

| 2003/0026809 A1 | 2/2003 | Robinson et al. |
| 2006/0240045 A1 | 10/2006 | Berthet et al. |
| 2019/0015528 A1 * | 1/2019 | Moran ................. A61K 9/0053 |

FOREIGN PATENT DOCUMENTS

WO     2004089408 A2     10/2004

OTHER PUBLICATIONS

Leonard et al (ACS Synth Biol. May 18, 2018; 7(5): 1279-1290).*
Powell et al (Proc Natl Acad Sci U S A. Nov. 29, 2016; 113(48): 13887-13892).*
PCT/US2020/18208, PCT Search Report & Written Opinion, dated Jun. 2, 2020, 8 pages.
Kwong, Waldan K. et al., Cultivation and characterization of the gut symbionts of honey bees and bumble bees: description of *Snodgrassella alvi* gen. nov., sp. nov., a member of the family Neisseriaceae of the Betaproteobacteria, and *Gilliamella apicola* gen. nov., sp. nov., a member of Orbaceae fam. nov., Orbales ord. nov., a sister taxon to the order 'Enterobacteriales' of the Gammaproteobacteria.
Abbasi, Jennifer, "New Hope for a Gonorrhea Vaccine", JAMA Sep. 12, 2017 vol. 318, No. 10, pp. 894-895.
CDC, "Sexually Transmitted Disease Surveillance 2012", Atlanta, GA: CDC 2013, 174 pages.
Gold, Ronald et al., "Carriage of Neisseria meningitidis and Neisseria lactamica in Infants and Children", The Journal of Infectious Diseases, vol. 137, No. 2, Feb. 1978, pp. 112-121, 10 pages, Abstract Only.
Hansen, J. et al., "Post-licensure safety surveillance study of routine use of quadrivalent meningoccal diphtheria toxoid conjugate vaccine", Vaccine 35 (2017) 6879-6884.
Jerse, Ann E. et al., "Estradiol-treated female mice as surrogate hosts for Neisseria gonorrhoeae genital tract Infections", Frontiers in Microbiology, Jul. 1, 2011, vol. 2, Article 107, 13 pages.
Jeyaprakash, A. et al., "Bacterial diversity in worker adults of Apis mellifera capensis and Apis mellifera scutellata (Insecta: Hymenoptera) assessed using 16S rRNA sequences", J Invertebr Pathol., Oct. 2003;84(2):96-103.
Kwong, Waldan K. et al., "Cultivation and characterization of the gut symbionts of honey bees and bumble bees: description of *Snodgrassella alvi* gen. nov., sp. nov., a member of the family Neisseriaceae of the Betaproteobacteria, and *Gilliamella apicola* gen. nov., sp. nov., a member of Orbaceae fam. nov., Orbales ord. nov., a sister taxon to the order 'Enterobacteriales' of the Gammaproteobacteria", International Journal of Systematic and Evolutionary Microbiology (2013), 63, 2008-2018.

(Continued)

*Primary Examiner* — Jennifer E Graser
(74) *Attorney, Agent, or Firm* — Timothy H. Van Dyke; WOLTER, VAN DYKE, DAVIS, PLLC

(57) ABSTRACT

Embodiments herein include an attenuated live vaccine composition for protection against *Neisseria* spp. infection, the vaccine composition comprising an effective amount of *Snodgras sella alvi* (*S. alvi*), or an antigen component thereof, and methods for treating or preventing disease related to or aggravated by *Neisseria gonorrhoea* is provided.

10 Claims, 5 Drawing Sheets

(56) References Cited

OTHER PUBLICATIONS

Li, Yanwen et al., "Immunization with Live Neisseria lactamica Protects Mice against Meningococcal Challenge and Can Elicit Serum Bactericidal Antibodies", Infection and Immunity, Nov. 2006, p. 6348-6355, vol. 74, No. 11.

Liu, Guangyu et al., "Non-pathogenic Neisseria: members of an abundant, multi-habitat, diverse genus", Microbiology (2015), 161, 1297-1312.

McQuillen, Daniel P. et al., "Complement-Mediated Bacterial Killing Assays", Methods in Enzymology, vol. 236, 1994, 137-147.

Petousis-Harris, Helen et al., "Effectiveness of group B outer membrane vesicle menigoccal vaccine against gonorrhoea in New Zealand: a retrospective case-control study", Lancet 2017; 390: 1603-1610.

Rice, Peter A. et al., "Neisseria gonorrhoeae: Drug Resistance, Mouse Models, and Vaccine Development", Annual Review of Microbiology, Annu. Rev. Microbiol., 2017, 71:665-686.

Rodrigues, Charlene M. C. et al., "Typing complex meningococcal vaccines to understand diversity and population structure of key vaccine antigens", Wellcome Open Research 2019, 3:15, 26 pages.

Sem chenko, Evgeny A. et al., "The Serogroup B Meningococcal Vaccine Bexsero ElicitsAntibodies to Neisseria gonorrhoeae", Clinical Infectious Diseases, 2019;69(7)1101-1111, Dec. 14, 2018.

Stratton, Charles W. "Serum Bactericidal Test", Clinical Microbiology Reviews, Jan. 1988, pp. 19-26, vol. 1, No. 1.

Suay-Garcia, Beatriz et al., "Future Prospects for Neisseria gonorrhoeae Treatment", Antibiotics 2018, 7, 49; 2018, 10 pages.

Tani, Chiara et al., "Quantification by LC-MS(E) of outer membrane vesicle proteins of the Bexsero® vaccine", Vaccine, Mar. 5, 2014;32(11):1273-1279.

WHO, "Control of Epidemic Meningococcal Disease", WHO Practical Guidelines. Geneva, Switz.: World Health Organ, 1998, 82 pages.

WHO, "Global Incidence and Prevalence of Selected Curable Sexually Transmitted Infections—2008", Geneva, Switz: World Health Organ, 2012, 28 pages.

Zielke, Ryszard A. et al., "Proteomics-driven Antigen Discovery for Development of Vaccines Against Gonorrhea", Molecular & Cellular Proteomics 15.7, pp. 2338-2355, Jul. 2016.

\* cited by examiner

Red - *S. alvi* Unstained
Blue - Pre-immunization sera
Green - *Post*-Immunization sera Red - *N. gonorrhea* Unstained
Blue - Pre-immunization sera
Green - Post-immunization sera

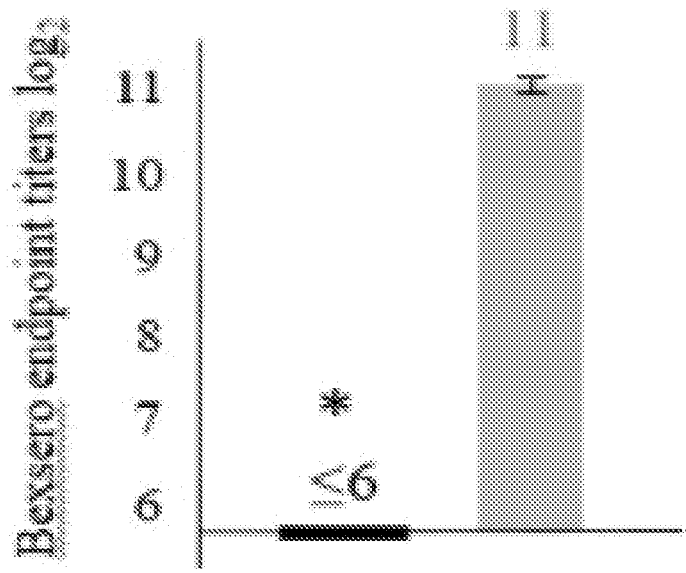
**Figure 8. Antisera raised against *S. alvi* react to components of meningococcal Bexsero vaccine.** ELISA plates were coated with Bexsero vaccine (5 μg/ml of protein) and probed with *S. alvi* antisera. Pre-bleeds drawn before immunization served as negative control. The difference is significant at *P=0.01.

HONEYBEE COMMENSAL *SNODGRASSELLA ALVI* VACCINE AGAINST PATHOGENIC *NEISSERIACEAE*

BACKGROUND

Currently, there are no vaccines to prevent gonorrhea. The catastrophic failure of clinical vaccine trials have discouraged further vaccine research in favor of antibiotic treatments. Recent projections; however, loom a scenario where *N. gonorrhoeae* develops multiple resistance at a pace faster than new antibiotics can be deployed. This scenario has fostered a renewed interest in the development of novel and effective vaccines.

SUMMARY

In an embodiment described herein, an attenuated live vaccine composition for protection against *Neisseria* spp. Infection is provided. The vaccine composition comprises an effective amount of *Snodgrassella alvi* (*S. alvi*), or an antigen component thereof.

In another embodiment, an attenuated live vaccine composition for enhancing production of antibodies against *Neisseria gonorrhoeae* is provided. The vaccine composition comprises an effective amount of *Snodgrassella alvi* (*S. alvi*), and optionally an adjuvant.

In still another embodiment, a method for immunizing a subject against *Neisseria* spp. infection is provided, the method includes administering to the subject an attenuated live vaccine composition for protection against *Neisseria* spp. Infection. The vaccine includes an effective amount of *Snodgrassella alvi* (*S. alvi*), or an antigen component thereof.

In yet another embodiment, a method of treating or preventing disease related to or aggravated by *Neisseria gonorrhoeae* infection in a subject in need thereof is provided. The method comprises administering to the subject a vaccine composition including an effective amount of *Snodgrassella alvi* (*S. alvi*), or an antigen component thereof.

BRIEF DESCRIPTION OF THE DRAWINGS

FIG. 8 shows Elisa test showing that post-immune sera raised against *S. alvi* detect epitopes of the meningococcal vaccine Bexsero.

DETAILED DESCRIPTION

Definitions

Figure 1:
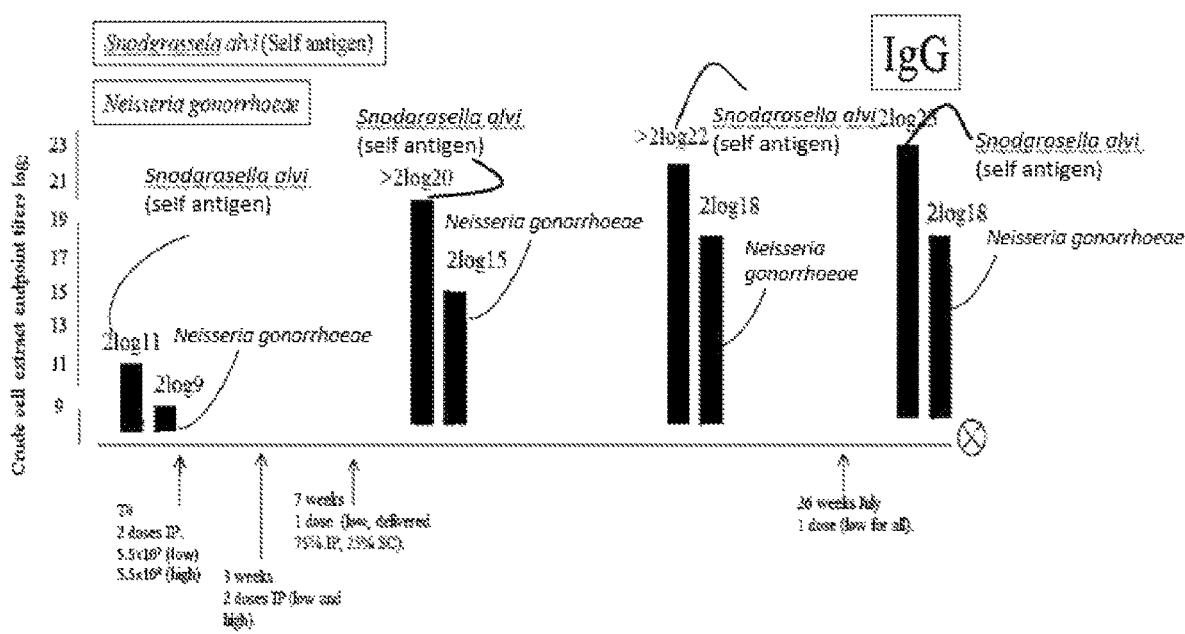
FIG. 1 provides a summary of immunization and resulting IgG titers as determined in ELISA test by coating the wells with 5 µg/ml of crude bacteria cell extract.

The term "administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like.

The term "attenuated" or "attenuation" as used herein refers to any treatment that disrupts or weakens the treated cell or strain. Attenuated or attenuation includes organisms that have been subjected to attenuation methods that reduce any potential residual virulence by imparting stable mutations, or methods to kill (i.e. via heat, radiation, chemical treatment, or otherwise) the organism, prior to administration of the treated cell or strain to the human, mammal, mammalian subject, animal, veterinary subject, placebo subject, research subject, experimental subject, cell, tissue, organ, or biological fluid.

As used herein, the term "vaccine" refers to compositions that affect the course of the disease by causing an effect on cells of the adaptive immune response, namely, B cells and/or T cells. The effect of vaccines can include, for example, induction of protective immunity. A vaccine can be used for therapeutic administration or prophylactic administration.

The compositions for therapeutic treatment described herein may be formulated for a select mode of administration including but not limited to parenteral (e.g. intravenously, subcutaneously, intradermally, or intramuscularly), topical, mucosal, e.g., vaginal, oral, nasal, or intraperitoneal. Preferably, the compositions are administered subcutaneously or intradermally, in non-limiting embodiments. In some embodiments, mucosal delivery provides for targeting the lymph nodes that drain the region by subcutaneous vaccination methods.

As used herein, the term "effective amount" refers to a quantity of a vaccine composition or an admixture that is sufficient to produce an intended biological effect.

Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

The terms "animal," "patient," or "subject," as used herein, mean any animal (e.g., mammals, (including, but not limited to humans, primates, dogs, cattle, cows, horses, kangaroos, pigs, sheep, goats, cats, rabbits, rodents, and transgenic non-human animals), and the like, which are to be the recipient of a particular treatment. Typically, the terms "animal" "subject" and "patient" are used interchangeably herein in reference to a human subject or a rodent. The preferred animal, patient, or subject is a human.

As used herein, the term "in conjunction" refers to synchronously or near synchronous timing. In conjunction as used herein may include within 1-10 days of administration (before, after and/or during) of standard treatment for *N. gonorrhoeae*, including but not limited to an antibiotic regimen, in a non-limiting embodiment.

Accordingly, an embodiment of the invention provides compositions for parenteral administration which comprise a solution comprising attenuated, live *S. alvi*, dissolved or suspended in an acceptable carrier, preferably an aqueous carrier. A variety of aqueous carriers may be used, e.g. water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use, or may be lyophilized. The lyophilized preparation may be combined with a sterile solution prior to administration. The composition embodiments may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, among others.

A human unit dose form of the composition is typically included and may comprise a human unit dose of an acceptable carrier. In one example, the acceptable carrier may include an aqueous carrier, and may be administered in a volume of fluid that is known by those skilled in the art to be used for administration of such compositions to humans (see, e.g., *Remington's Pharmaceutical Sciences*, 17$^{th}$ Edition, A. Gennaro, Editor, Mack Publishing Co., Easton, Pa., 1985, incorporated herein by reference).

Overview

A decrease in treatment options for *Neisseria gonorrhoeae* infections has made this sexually transmitted disease (STD) a major health concern. The plasticity of its genome allows bacteria to evade immune surveillance and to develop antibiotic resistance at a pace that is projected to make *Neisseria gonorrhoeae* infections untreatable in the near future. World-wide reports of new cases are in excess of 100 million cases. Currently there are no vaccines to effectively prevent and/or treat gonorrhea. It has been observed that the meningococcal vaccine, MeNZB, may confer partial cross-protection against *Neisseria gonorrhoeae*. The underlying mechanism of cross-protection is based on the homology between *N. gonorrhoeae* and *N. meningitidis* antigens.

It is believed that honey bees are highly dependent on their hive-mates for acquisition of their normal gut bacteria. Each worker bee acquires a fully expanded, typical gut community before it leaves the hive. Different colonies may maintain distinct community profiles at the strain level and thus, biological variation among colonies results, in part, from variation in gut communities. Worker bees ("workers") develop a characteristic core microbiota within hives. Some gram-positive members of the core microbiota can be acquired through contact with hive surfaces. Gram-negative species, *Snodgrassella alvi, Gilliamella apicola*, and *Frischella perrara*, appear to be acquired through contact with nurse bees or with fresh feces but not through oral trophallaxis. The eusocial honey bees and bumble bees harbor two specialized gut symbionts, *Snodgrassella alvi* and *Gilliamella apicola*, and these microorganisms are specific to bees, with different strains of these bacteria assorting to host species.

Workers initially lack gut bacteria. Within 4-6 days within hives, workers gain large characteristic communities of gut bacteria in the ileum and rectum. The core species of gram-negative bacteria, *S. alvi, G. apicola*, and *F. perrara*, are believed to be conveyed via nurses or hindgut material, whereas some gram-positive species are often transferred through exposure to hive components. *G. apicola* and *S. alvi* are mutualistic symbionts with roles in both pathogen defense and nutrition. Their highly restricted distribution and phylogenetic correlation with their hosts are suggestive of a lengthy coevolutionary history with bees and with each other.

As previously mentioned, Neisseriaceae colonize a wide panel of vertebrate and invertebrate animals including honeybees. A close look into the honeybee Gammaproteobacteria revealed that they belong to a species *S. alvi*. *S alvi* branches within the family Neisseriaceae, thus being a sister genus to *Neisseria, Kingella*, and *Eikenella*. Observations have shown that between *S. alvi* and Neisseriaceae, the overall protein identity and similarity range between 40-60% and 60-90%, respectively, thus straddling the boundary of genus demarcation.

Consequently, it has been found herein that the honeybee obligate commensal *S. alvi* is an effective naturally attenuated live-vaccine platform to generate protective immunity against *Neisseria* pathogens including *N. gonorrhoeae*.

In particular, embodiments described herein include the honey bee obligate commensal *S. alvi* as a biologically-contained, live vaccine for generating protective immunity against *N. gonorrhoeae*.

In an embodiment herein, *S. alvi* has been deployed as a naturally attenuated, non-pathogenic live vaccine against *N. gonorrhoeae* infection. The term "naturally attenuated" as used herein includes, for example, *S. alvi* in its natural state without subjecting it to convention attenuation methods, since it does not naturally infect mammals. However, alternatively, the organism could be subjected to further attenuation methods, i.e., reduce virulence by imparting stable mutations, or methods to kill (i.e. via heat, radiation, chemical treatment, etc.) the organism, prior to administration. In this case, the vaccine would be considered to be "attenuated."

The meningococcal vaccine MeNZB provides partial cross-protection against gonorrhea. The MeNZB found to provide partial cross-protection against gonorrhea was comprised of OMV (outer membrane vesicles) whose composition was poorly defined. *N. gonorrhoeae* and *N. meningitidis* are closely related and therefore, some of the MeNZB components induce cross-protection against *N. gonorrhoeae* due to antigen homology. MeNZB; however, is no longer available as a vaccine. Its successor, 4CMenC has a well-defined 4-protein antigen composition plus a panel of accessory components.

Because *N meningitidis* and *N. gonorrhoeae* share protein identity of >95% and because a vaccine raised against *N meningitidis* can confer cross protection against *N. gonorrhoeae*, it is hypothesized that the immunity raised by *S. alvi* will extend both to *N. gonorrhoeae* and *N meningitidis*. The data provided in FIG. 8 shows that the post-immune sera from mice immunized with *S. alvi* wkB12 recognize at least some components of the meningococcal vaccine Bexsero.

Turning to the Figures, FIG. 1 is a table providing a listing of various proteins of *S. alvi*. FIG. 1 compares the listed proteins of *S. alvi* to their homologs in both *N. meningitidis* MC58 (a hypervirulent strain which is commonly used in mouse challenges) and *N. gonorrhoeae* FA1090 (a strain that is used in a human model of urethra infection). Homologies to components of 4CMenC have been identified herein, and are indicated in FIG. 1. These findings provide additional support for the vaccine embodiments described herein including vaccines against *N. gonorrhoeae*. Combinations of the *S. alvi* proteins have been identified herein for use as antigen compositions for vaccine embodiments for *N. gonorrhoeae*.

The discovery that a vaccine designed against one species of *Neisseria* can cross-protect against a related pathogen is further supported by the finding that some strains of the commensal *Neisseria lactamica* can trigger antigen recognition and induce serum bactericidal activity (SBA) against some strains of *N. meningitidis*. However, several considerations discourage implementation of *N. lactamica*, or other commensal Neisseriae, as a live vaccine vectors against their pathogenic congeners. For example, longitudinal studies linked early colonization by *N. lactamica* to protection against later infections by *N. meningitidis*. Moreover *N. lactamica*, as well as virtually all Neissericeae tested so far can become opportunistic pathogens.

EXAMPLES

Materials and Methods

A panel of microorganisms including an array of lactic acid bacteria, *Gilliamella apicola*, *Bifidobacterium asteroides* as well as *Snodgrassella alvi* which branches within the family Neisseriaceae were isolated from honey bee workers. *Snodgrassella alvi* was used to immunize mice in experiments described herein.

Mice were initially immunized by the intraperitoneal (IP) route with alternatively $\times 10^7$ or $5 \times 10^8$ CFUs of *S. alvi* wkB12, and at week 3, boosted IP with a high dose with $5 \times 10^7$ CFUs. This regimen proved to be safe for the immunized mice. At week 7, mice were given a second boost using $5 \times 10^7$ CFUs, which was delivered 75% IP and 25% subcutaneously. Mice received a final IP immunization at week 26 as shown in (FIG. 1). IgG titers were determined for mice immunized with *S. alvi* wkB12 for an extended period of time.

Example 1: Naturally Attenuated *S. alvi* Confers Protection Against *Neisseria gonorrhoea*

FIG. 1 provides a summary of immunization with *S. alvi* and resulting IgG titers as determined in an ELISA test by coating the wells with 5 mg/ml of crude bacteria cell extract. The data provided in FIG. 1 demonstrates that the induced immunity is long-lasting, remarkably elevated, and a value range that would confer protection against *Neisseria gonorrhoea*.

Figure 2:
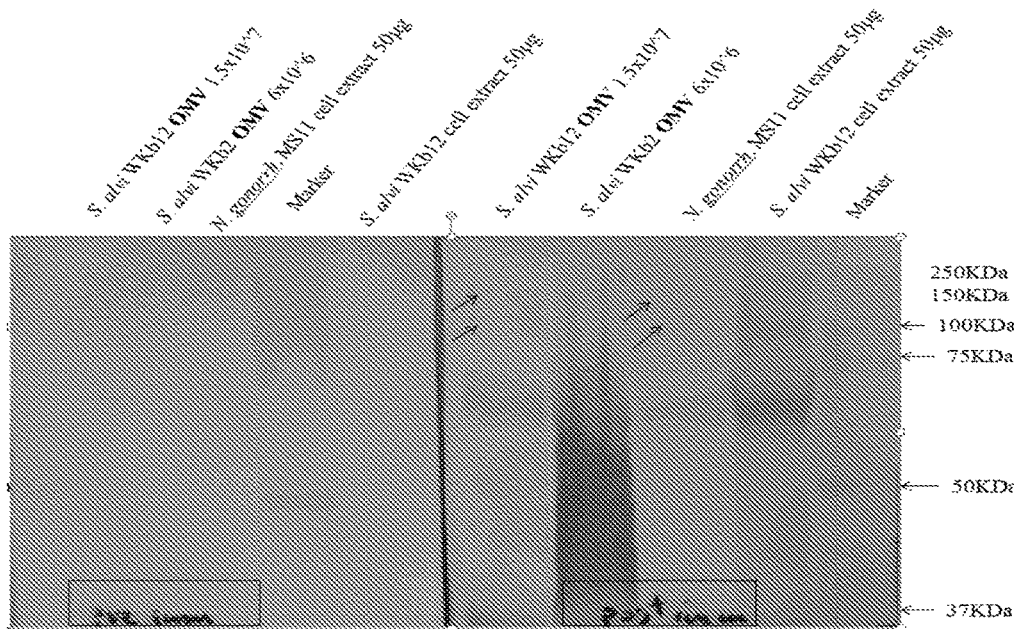
FIG. 2 shows the results of a Western blot where crude extracts from different bacteria and purified outer membrane vesicles (OMVs) were blotted onto a nitrocellulose membrane and probed with pre- and post-immune sera.

Example 2: *S. alvi* OMV Antigens Detected by Sera Generated Against Crude Cell Extracts It was also tested herein whether the IgG immune response generated against crude cell extracts would extend to antigens carried on *S. alvi* outer membrane vesicles (OMV). Data represented in FIG. 2 demonstrates that antigens borne on the *S. alvi* OMVs are detected by sera generated against crude cell extracts. FIG. 2 shows the results of a Western blot where crude extracts from different bacteria and purified outer membrane vesicles (OMVs) were blotted onto a nitrocellulose membrane and probed with pre- and post-immune sera.

Example 3: Proposed Vaccine Regimen Results in Significant Serum Bactericidal Activity Against *N. gonorrhoeae* Strain MS11

A serum bactericidal activity (SBA) test was used to evaluate whether the high IgG titers were linked to protective immunity. SBA is regularly used to evaluate the protective activities of vaccination procedures against a wide panel of pathogens (14, 15), particularly for human pathogenic *N. meningitidis* and *N. gonorrhoeae* for which technical and regulatory issues hamper in vivo challenge (15-17). *N. gonorrhoeae* strain MS11 (a standard strain used in vaccine development) was streaked on Gonococci Base solid medium and grown overnight. The following morning bacteria were scraped off the plate, resuspended at $OD_{600}$~0.1 in the same medium without agar and grown with vigorous shaking for 2 hours before use. The proper concentration of bacteria, the dilution of the baby rabbit complement (BioRad), and the dilution of the antisera were determined experimentally. The data presented in FIG. 3 was generated by pooling antisera (pre-bleeds and terminal bleeds) from 16 mice.

Figure 3:
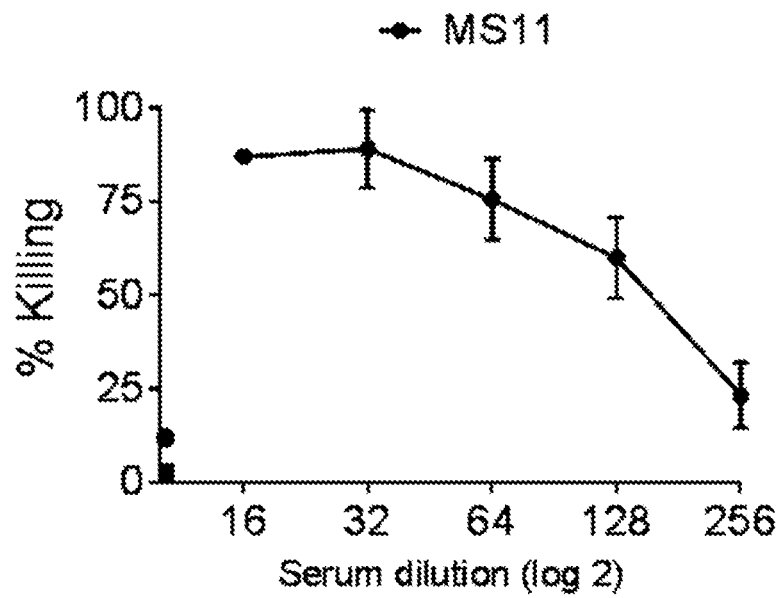
FIG. 3 provides the results of a serum bactericidal activity test.

The results of the serum bactericidal activity test are shown in FIG. 3. The killing percentage of serial two-fold dilutions of pooled terminal bleeds (n=16) was determined by the subtraction of corresponding dilutions of pre-bleeds taken from the same mice. The results depict five experiments conducted with these sera at four different times. The black circle shows the complement-only (no antisera) killing control. The black square shows antisera only without the addition of complement (no complement) control.

The data demonstrates that the example vaccination regimen described herein induces significant SBA against *N. gonorrhoeae* strain MS11 (a standard strain used in vaccine development). The minimum dilution universally recognized as being protective is 1:4, whereas herein protection was achieved at 1:128 dilution with some SBA still clearly detectable at 1:256 dilution. The protection conferred by native *S. alvi* is less than 2 $\log_2$ lower than those reported in the literature for subunit vaccines, which have been selected in silico (16, 17).

Example 4: *S. alvi* wkB12 Shows Cross Hybridization with *N. gonorrhoeae* MS11

Figure 4:
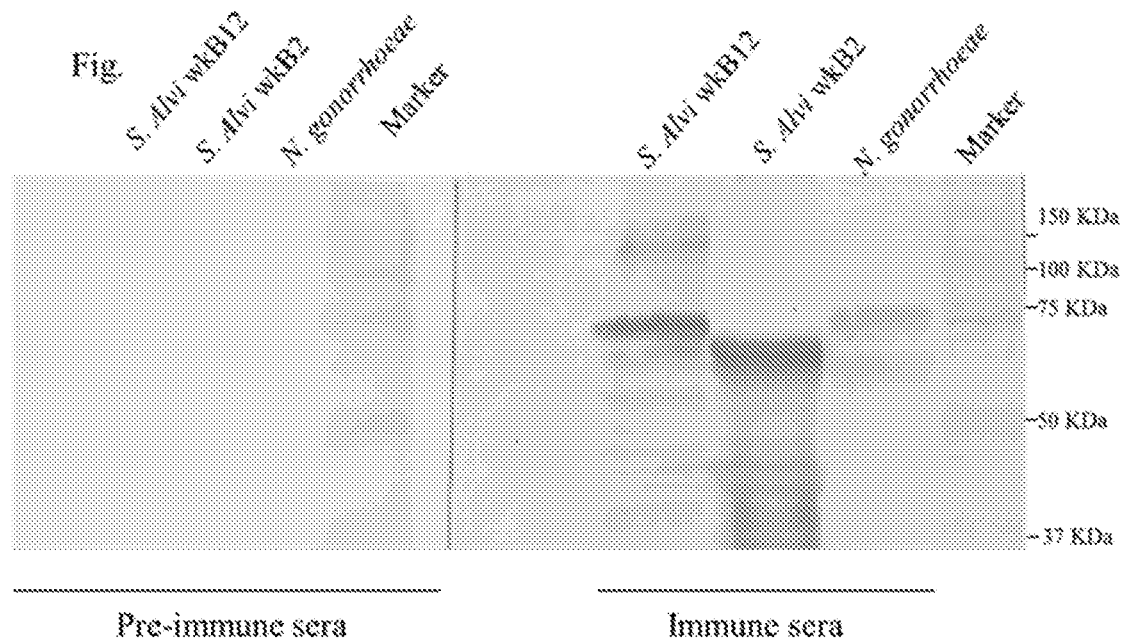
FIG. 4 shows the results of a Western blot where crude extracts from different bacteria were blotted onto a nitrocellulose membrane and probed with pre- and post-immune sera. This experiment is a partial and improved version of what is shown in FIG. 2.

As shown in the results displayed in FIG. 4, fifteen BALB/c mice were immunized 3 times intraperitoneally with ($5 \times 10^7$ or $5 \times 10^8$ CFUs) *S. alvi* wkB12, and their pre-bleed and antisera were used herein. Crude protein extract probed with sera from mice immunized with live *S. alvi* wkB12 showing cross-hybridization with *N. gonorrhoeae* MS11. This experiment shows that sera raised against *S. alvi* wkB12 can recognize antigens of *N. gonorrhoeae*. There is no reactivity before immunization, thus proving that the immunization process is responsible for the reactivity. As expected the reactivity against the immunizing antigen, *S. alvi* wkB12, is higher than that raised against the partially homologous antigen, *N. gonorrhoeae*.

Example 5

Figure 5:
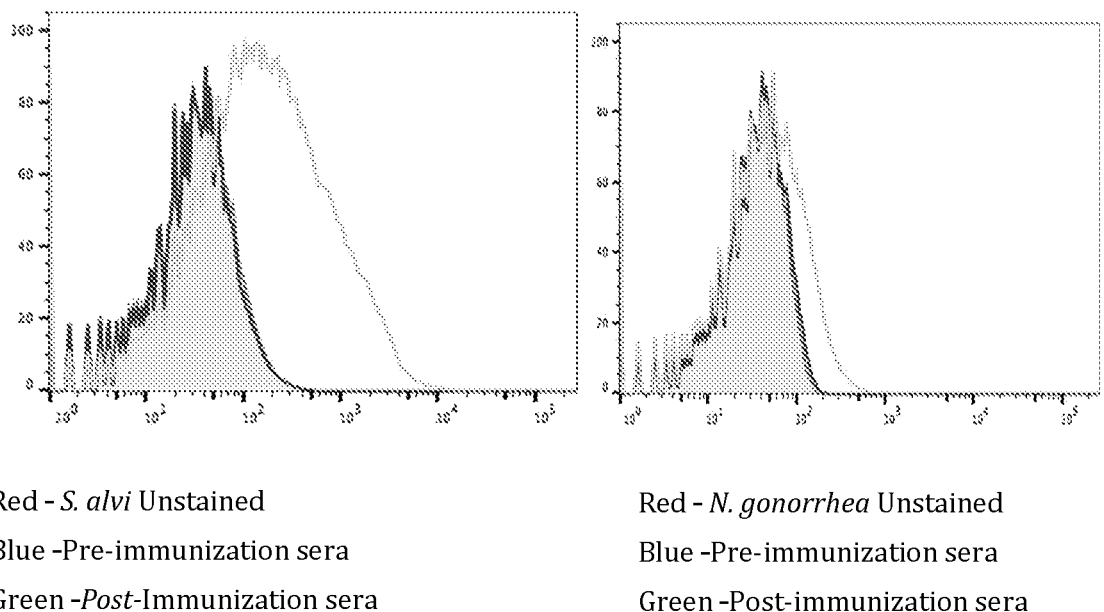
FIG. 5 shows the results of detection by flow cytometry of cross-reactive epitopes on the surface of *S. alvi* wkB12 and *N. gonorrhoeae* MS11.

FIG. 5 shows the results of detection by flow cytometry of cross-reactive epitopes on the surface of *S. alvi* wkB12 and *N. gonorrhoeae* MS11. Bacteria were reacted with sera, washed and decorated with FITC-conjugated goat anti-mouse IgG antibodies. This experiment confirms with a different technique what is shown in FIG. 4. It also shows that some of the cross-reactive epitopes are displayed on the surface, of the bacteria. As expected the reactivity against the immunizing antigen, *S. alvi* wkB12, is higher than that raised against the partially homologous antigen, *N. gonorrhoeae*.

Example 6: IgG Titers Increased Significantly in Mice Immunized with *S. alvi* when Challenged with *N. gonorrhoeae*

Figure 6:
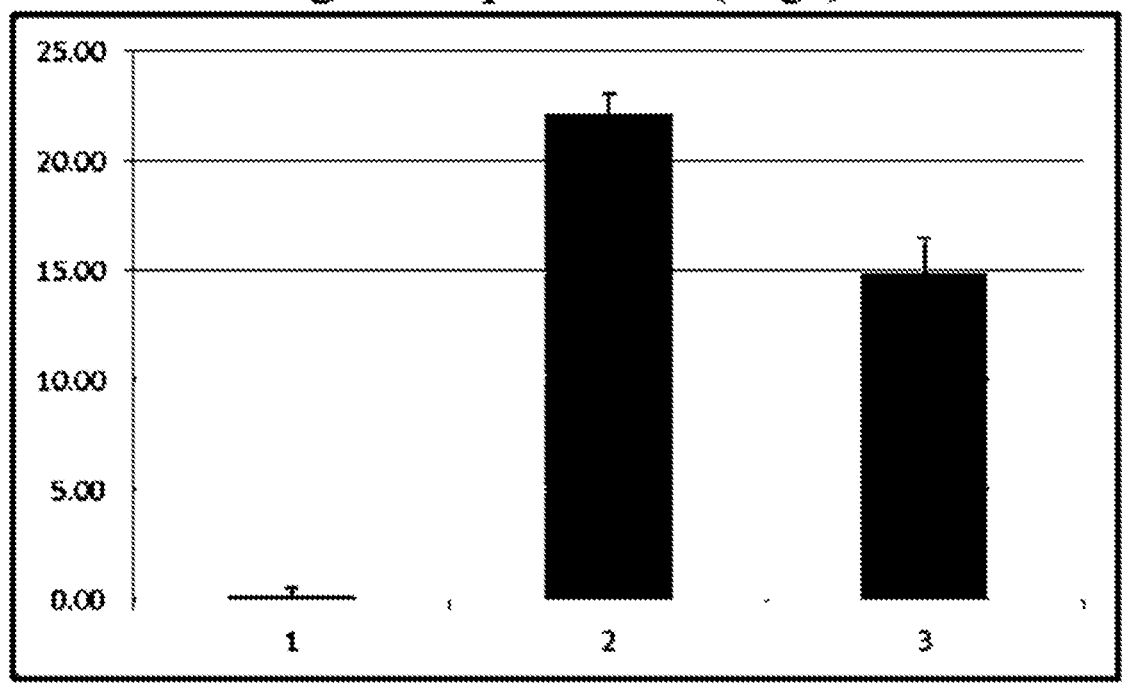
FIG. 6 shows a graphical representation of an ELISA test where wells were post-immune sera of mice immunized with *S. alvi* wkB12 were used to probe wells coated with different antigens as follows. (1) bovine serum albumin, BSA), (2) *S. alvi* wkB12 extract, (3) *Neisseria gonorrhoeae*.

FIG. 6 shows antibody titers in mice immunized with *S. alvi* wkB12. ELISA plates were coated with 1) an irrelevant antigen (BSA), 2) an *S. alvi* crude extract or 3) a *N. gonorrhoeae* crude extract and then probed with diluted sera. All antigens were used at 5 µg/ml protein. FIG. 6 represents an antibody response is triggered in recipient mice when immunized with *S. alvi* and exposed to *N. gonorrhoeae*. This experiment confirms what is shown in FIG. 1 and it introduces a further stringent control. In fact ELISA wells coated with an irrelevant antigen, bovine serum albumin, do not react when probed with post-immune sera from mice immunized with *S. alvi* wkB12. On the contrary wells coated with a crude extract of, alternatively, *S. alvi* wkB12 or *N. gonorrhoeae* react accordingly to the homology of the extracts to the immunizing antigen (*S. alvi* wkB12).

Example 7

Figure 7:
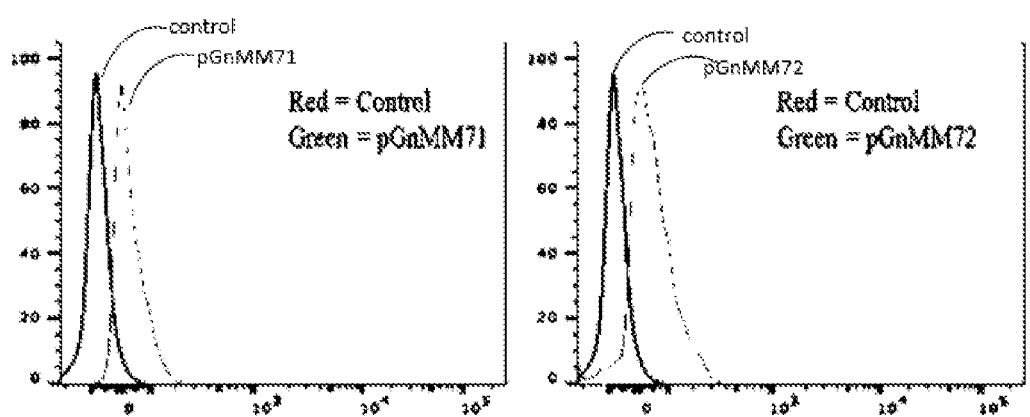
FIG. 7 shows two integrative vectors, pGnMM71 and pGnMM72 expressing the fluorescent protein m-Cherry, transformed into *S. alvi* wkB12.

FIG. 7 shows two integrative vectors, pGnMM71 and pGnMM72 expressing the fluorescent protein m-Cherry, transformed into *S. alvi* wkB12 in preparation for the expression of *N. gonorrhoeae* protective antigens. The data shows the shift in fluorescence of bacteria previously selected on Kanamycin, the marker borne on the vector backbone. This experiment shows that *S. alvi* wkB12 is amenable of genetic manipulation. This observation paves the way to a panel of interventions where protective antigens from *N. gonorrhoeae* or *N. meningitidis* can be engrafted into *S. alvi* to improve its efficacy. Also some protein adjuvants, such as FliC from *Salmonella typhimurium* can be expressed to improve the immunogenicity of the vaccine vector, *S. alvi*.

*Snodgrassella alvi* (strains wkB12, pAJ198, or wkB2) are well tolerated in recipient mice and is able to trigger a robust antibody response. This response can be compared to that of *Salmonella* vaccines. The immune reaction against *Snodgrassella alvi* shown in the Examples herein demonstrates a robust cross-reaction against *Neisseria gonorrhoeae* MS11. Results provided herein demonstrates that in one embodiment, protective immunity to *N. gonorrhoeae* can be elicited subsequent vaccination of mice with *S. alvi*.

In one embodiment described herein, an attenuated live vaccine composition for protection against *Neisseria* spp. infection is provided. The vaccine composition may include an effective amount of *Snodgrassella alvi* (*S. alvi*) or an antigen component thereof, and optionally an adjuvant. In a further embodiment, the vaccine composition comprises between $5 \times 10^4$-$5 \times 10^8$ CFUs of *S. alvi* wkB12. In an alternative embodiment, the *S. alvi* employed comprises killed bacteria and or DOMV (Detergent-extracted outer membrane vesicles) as in the 4CMenB (Bexsero). In an alternative embodiment, *S. alvi* is used as a scaffold to express protective antigens (instead of producing them in *E. coli* and aggregate the recombinant proteins into DOMV, as in for example, the production of 4CMenB).

In another embodiment, an attenuated live vaccine composition for enhancing production of antibodies against *Neisseria* spp. infection is provided. The vaccine composition may include an effective amount of *Snodgrassella alvi* (*S. alvi*), and optionally, an adjuvant.

In yet another embodiment, a method for immunizing a subject against *Neisseria* spp. infection is provided. The method includes administering to the subject a vaccine composition including an effective amount of *Snodgrassella alvi* (*S. alvi*) and optionally, an adjuvant. In an embodiment, the method includes immunization against the pathogenic bacteria *Neisseria gonorrhoeae*. The vaccine composition may include killed bacteria or microbial extracts, and sometime combined with suitable adjuvant. Either composition of the vaccine may be administered to the subject up to four separate immunizations, in one embodiment. In another embodiment, the vaccine may be administered to the subject in at least three (3) immunizations. In yet another embodiment, the vaccine may be administered to the subject in at least two (2) immunizations.

In one non-limiting embodiment, each dose includes between $5 \times 10^7$ and $5 \times 10^8$ CFUs of *S. alvi* wkB12. The administration may occur intraperitoneally (IP) or subcutaneously (subQ), or a combination thereof. In one example, the first, second and third doses are administered intraperitoneally. In one embodiment, at first immunization $T_0$ (i.e., week one) two doses of the vaccine composition are delivered to the subject, wherein the first dose includes $5 \times 10^7$ CFUs of *S. alvi* wkB12, and the second dose includes $5 \times 10^8$ CFUs of *S. alvi* wkB12. At three weeks post $T_0$, in one embodiment, two doses of the vaccine are administered to the subject as in week one at $T_0$ ($5 \times 10^7$ CFUs of *S. alvi* wkB12, and the second dose includes $5 \times 10^8$ CFUs of *S. alvi* wkB12). The immunizations administered at weeks 7 and 26 post $T_0$ include one dose. In one embodiment, 75% of the 7-week dose is administered intraperitoneally, and 25% of the fourth dose is administered subcutaneously, for example. In one non-limiting embodiment, the doses are administered at weeks 1, 3, 7, and 26.

REFERENCES

1. WHO. 1998. Control of Epidemic Meningococcal Disease. WHO Practical Guidelines. Geneva, Switz.: World Health Organ.
2. WHO. 2012. Global Incidence and Prevalence of Selected Curable Sexually Transmitted Infections—2008. Geneva, Switz: World Health Organ.
3. CDC. 2013. Sexually Transmitted Disease Surveillance 2012.Atlanta, GA: CDC.
4. https://www.cdc.gov/drugresistance/threat-report-2013/5.
5. Suay-García B, Pérez-Gracia M T. Future Prospects for *Neisseria gonorrhoeae* Treatment. Antibiotics (Basel). 2018 Jun. 15; 7(2). pii: E49. doi: 10.3390/antibiotics7020049.
6. Hansen J, Zhang L, Eaton A, Baxter R, Robertson C A, Decker M D, Greenberg D P, Bassily E, Klein N P. Post-licensure safety surveillance study of routine use of quadrivalent meningococcal diphtheria toxoid conjugate vaccine (MenACWY-D) in infants and children. Vaccine. 2018 Apr. 12; 36(16):2133-2138. doi: 10.1016/j.vaccine.2018.02.107.
7. Petousis-Harris H, Paynter J, Morgan J, Saxton P, McArdle B, Goodyear-Smith F, Black S. Effectiveness of a group B outer membrane vesicle meningococcal vaccine against gonorrhoea in New Zealand: a retrospective case-control study.
Lancet. 2017 Sep. 30; 390(10102):1603-1610. doi: 10.1016/S0140-6736(17)31449-6. Epub 2017 Jul. 10.
8. Abbasi J. New Hope for a Gonorrhea Vaccine. JAMA. 2017 Sep. 12; 318(10):894-895
9. Li Y, Zhang Q, Winterbotham M, Mowe E, Gorringe A, Tang C M. Immunization with live *Neisseria lactamica* protects mice against meningococcal challenge and can elicit serum bactericidal antibodies. Infect Immun. 2006 November; 74(11):6348-55.
10. Liu G, Tang C M, Exley R M. Non-pathogenic *Neisseria*: members of an abundant, multi-habitat, diverse genus. Microbiology. 2015 July; 161(7):1297-312.
11. Gold R, Goldschneider I, Lepow M L, Draper T F, Randolph M. Carriage of *Neisseria meningitidis* and *Neisseria lactamica* in infants and children. J Infect Dis. 1978 February; 137(2):112-21.
12. Jeyaprakash A, Hoy M A, Allsopp M H. Bacterial diversity in worker adults of *Apis mellifera capensis* and *Apis mellifera scutellata* (Insecta: *hymenoptera*) assessed using 16S rRNA sequences. J Invertebr Pathol. 2003 October; 84(2):96-103.
13. Kwong W K, Moran N A. Cultivation and characterization of the gut symbionts of honey bees and bumble bees: description of *Snodgrassella alvi* gen. nov., sp. nov., a member of the family Neisseriaceae of the Betaproteobacteria, and *Gilliamella apicola* gen. nov., sp. nov., a member of Orbaceae fam. nov., Orbales ord. nov., a sister taxon to the order 'Enterobacteriales' of the Gammaproteobacteria. Int J Syst Evol Microbiol. 2013 June; 63(Pt 6):2008-18.
14. Stratton C W. Serum bactericidal test. Clin Microbiol Rev. 1988 January; 1(1):19-26. Review.
15. McQuillen D P, Gulati S, Rice P A. Complement-mediated bacterial killing assays. Methods Enzymol. 1994; 236:137-47.
16. Rice P A, Shafer W M, Ram S, Jerse A E. *Neisseria gonorrhoeae*: Drug Resistance, Mouse Models, and Vaccine Development. Annu Rev Microbiol. 2017 Sep. 8; 71:665-686.
17. Zielke R A, Wierzbicki I H, Baarda B I, Gafken P R, Soge O O, Holmes K K, Jerse A E, Unemo M, Sikora A E. Proteomics-drivenAntigenDiscoveryforDevelopmentofVaccinesAgainstGonorrhea. Mol Cell Proteomics. 2016 July; 15(7):2338-55.
18. Tani C, Stella M, Donnarumma D, Biagini M, Parente P, Vadi A, Magagnoli C, Costantino P, Rigat F, Norais N. Quantification by LC-MS(E) of outer membrane vesicle proteins of the Bexsero® vaccine. Vaccine. 2014 Mar. 5; 32(11):1273-9.
19. Rodrigues C M C, Chan H, Vipond C, Jolley K, Harrison O B, Wheeler J, Whiting G, Feavers I M, Maiden M C J. Typing complex meningococcal vaccines to understand diversity and population structure of key vaccine antigens. Wellcome Open Res. 2018 Nov. 29; 3:151.
20. Semchenko E A, Tan A, Borrow R, Seib K L. The serogroup B meningococcal vaccine Bexsero elicits antibodies to *Neisseria gonorrhoeae*. Clin Infect Dis. 2018 Dec. 14.
21. Jerse A E, Wu H, Packiam M, Vonck R A, Begum A A, Garvin L E. Estradiol-Treated Female Mice as Surrogate Hosts for *Neisseria gonorrhoeae* Genital Tract Infections. Front Microbiol. 2011 Jul. 1; 2:107.

What is claimed is:

1. A method for immunizing a subject against *Neisseria gonorrhoeae* infection, comprising administering to the subject an attenuated live vaccine composition for protection against *Neisseria gonorrhoeae* infection, the vaccine composition comprising an effective amount of *Snodgrassella alvi* (*S. alvi*), and an adjuvant.

2. The method of claim 1, wherein the vaccine is administered to the subject in four (4) doses.

3. The method of claim 2, wherein each dose comprises between $5 \times 10^4$ and $5 \times 10^9$ CFUs of *S. alvi*.

4. The method of claim 1, wherein the administration occurs intraperitoneally (IP), intradermally (ID), intramuscularly (IM), or subcutaneously (subQ), intranasally, intraorally, intravaginally, or via the para-genito-urinary tract, or a combination thereof.

5. The method of claim 4, wherein the first and second doses are administered parenterally, by intradermal, intramuscular, subcutaneous administration, or by intraperitoneal administration.

6. The method of claim 4, wherein 75% of the third dose is administered intraperitoneally, and 25% of the third dose is administered subcutaneously.

7. The method of claim 2, wherein the doses are administered at weeks 1, 3, 7, and 26.

8. A method of treating or preventing disease related to or aggravated by *Neisseria gonorrhoeae* infection in a subject in need thereof comprising administering to the subject a composition comprising an attenuated live vaccine composition for protection against *Neisseria gonorrhoeae* infection, the vaccine composition comprising an effective amount of *Snodgrassella alvi* (*S. alvi*), and an adjuvant.

9. The method of claim 1, wherein the *S. alvi* strain comprises wkB12, pAJ198, or wkB2.

10. The method of claim 1, wherein the adjuvant comprises a toll-like receptor (TLR) agonist, comprising, MPL, alum, or a combination thereof.

* * * * *